(12) United States Patent
Kwon et al.

(10) Patent No.: US 9,527,111 B2
(45) Date of Patent: Dec. 27, 2016

(54) WAVEGUIDE FOR A BULK-TYPE MEDIUM, VIBRATOR USING SAME TO TRANSMIT SHEAR WAVES TO A BULK-TYPE MEDIUM, AND METHOD USING THE VIBRATOR TO TRANSMIT SHEAR WAVES TO A BULK-TYPE MEDIUM

(71) Applicants: Young Eui Kwon, Seoul (KR); Hyun Joong Jeon, Seoul (KR); Hoe Woong Kim, Seoul (KR); Yoon Young Kim, Seoul (KR)

(72) Inventors: Young Eui Kwon, Seoul (KR); Hyun Joong Jeon, Seoul (KR); Hoe Woong Kim, Seoul (KR); Yoon Young Kim, Seoul (KR)

(73) Assignee: SNU R&DB FOUNDATION, Seoul (KR)

( * ) Notice: Subject to any disclaimer, the term of this patent is extended or adjusted under 35 U.S.C. 154(b) by 373 days.

(21) Appl. No.: 14/350,012

(22) PCT Filed: Oct. 5, 2012

(86) PCT No.: PCT/KR2012/008058
§ 371 (c)(1),
(2) Date: Apr. 4, 2014

(87) PCT Pub. No.: WO2013/051874
PCT Pub. Date: Apr. 11, 2013

(65) Prior Publication Data
US 2014/0246954 A1    Sep. 4, 2014

(30) Foreign Application Priority Data

Oct. 7, 2011 (KR) .......................... 10-2011-0102652

(51) Int. Cl.
*B06B 1/06* (2006.01)
*B06B 1/08* (2006.01)
(Continued)

(52) U.S. Cl.
CPC ............... *B06B 3/00* (2013.01); *B06B 1/0644* (2013.01); *B06B 1/08* (2013.01); *G01N 29/2412* (2013.01);
(Continued)

(58) Field of Classification Search
CPC ... G01N 29/043; G01N 29/221; G01N 29/2412; G01N 29/2462; G01N 2291/0422; B06B 1/0644; B06B 1/08; B06B 3/00; B06B 2201/54; B06B 2201/55; B06B 2201/58; B06B 1/0648; G10K 11/02; G10K 11/025; G10K 11/355
(Continued)

(56) References Cited

U.S. PATENT DOCUMENTS 3,512,400 A * 5/1970 Lynnworth .......... G01N 29/041
73/597
4,735,097 A * 4/1988 Lynnworth ............. G01F 1/662
73/290 V
(Continued)

FOREIGN PATENT DOCUMENTS

KR    10-2010-0111986    10/2010
KR    10-2010-0126950    12/2010
(Continued)

OTHER PUBLICATIONS

Written Opinion-PCT/KR2012/008058 dated Feb. 22, 2013.
International Search Report-PCT/KR2012/008058 dated Feb. 22, 2013.

*Primary Examiner* — Barbara Summons
(74) *Attorney, Agent, or Firm* — Cantor Colburn LLP

(57) ABSTRACT

The aim of the present invention is to provide a waveguide capable of transmitting shear waves in a desired pattern to a bulk-type medium, a vibrator, and a method of transmitting shear waves by using the vibrator. To this end, the present invention provides a waveguide including a vibrating por-
(Continued)

tion that is vibrated by a vibrating unit, a transmitting portion that transmits shear waves generated by the vibrating unit to a bulk-type medium and is thicker than the vibrating portion, and a connecting portion that contacts both the vibrating portion and the transmitting portion and has a thickness varying from a portion contacting the vibrating portion to a portion contacting the transmitting portion. Also, the present invention provides a vibrator using the waveguide and a method of transmitting shear waves by using the vibrator.

13 Claims, 20 Drawing Sheets

(51) Int. Cl.
    *B06B 3/00*         (2006.01)
    *G01N 29/24*     (2006.01)
    *G10K 11/35*     (2006.01)

(52) U.S. Cl.
    CPC ......... *G01N 29/2462* (2013.01); *G10K 11/355* (2013.01); *G01N 2291/0422* (2013.01)

(58) Field of Classification Search
    USPC ........ 333/141, 145, 147, 148, 149; 310/311, 310/323.01, 323.19, 326–328, 334, 26, 310/12.24, 310/152, 154.01, 154.02; 73/598, 644, 866.5
    See application file for complete search history.

(56) References Cited

U.S. PATENT DOCUMENTS

| | | | | | |
|---|---|---|---|---|---|
| 5,159,838 | A | * | 11/1992 | Lynnworth | ............... B06B 3/00 73/644 |
| 5,828,274 | A | * | 10/1998 | Jen | ......................... G10K 11/24 333/143 |
| 8,090,131 | B2 | * | 1/2012 | Lynnworth | ............ G10K 11/24 381/338 |
| 2010/0244591 | A1 | * | 9/2010 | Cho | ...................... H01L 41/125 310/26 |
| 2011/0159461 | A1 | * | 6/2011 | Mourad | ............. A46B 15/0002 433/216 |

FOREIGN PATENT DOCUMENTS

| | | |
|---|---|---|
| KR | 10-2010-0137770 | 12/2010 |
| KR | 10-2011-0055881 | 5/2011 |

* cited by examiner

WAVEGUIDE FOR A BULK-TYPE MEDIUM, VIBRATOR USING SAME TO TRANSMIT SHEAR WAVES TO A BULK-TYPE MEDIUM, AND METHOD USING THE VIBRATOR TO TRANSMIT SHEAR WAVES TO A BULK-TYPE MEDIUM

TECHNICAL FIELD

The present invention relates to a waveguide for a bulk-type medium, a vibrator that transmits shear waves to a bulk-type medium using the waveguide, and a method of transmitting shear waves by using the vibrator, and more particularly, to a waveguide that can cut off shear waves of higher-order modes generated from a vibrating unit and transmit shear waves of a first mode only, a vibrator that can transmit shear waves in a desired pattern to a bulk-type medium by using the waveguide, and a method of transmitting shear waves to a bulk-type medium by using the vibrator.

The present invention was derived from research conducted by Creative Research Support Project, Leap Research Support Project, and High Nondestructive Testing Technology Development Project of the Korea Science and Engineering Foundation and Seoul National University Research and Development Business Foundation.

[20100019241, Multiscale Paradigm for Creative Design of Multiphysical Complex Structure Systems]

[20110017445, Elasto-vibro-acoustic wave tailoring by meta phenomena of waves]

[20110030113, Development of the magneto-mechanical ultrasonic guided wave transducer system for NDE of pipes in the nuclear power plant]

BACKGROUND ART

Much research has been conducted into methods of transmitting shear waves by vibrating a plate member or a rod member. In general, the research employs a method of directly transmitting shear waves to a member to be vibrated by using a vibrating unit that generates a vibratory force.

However, when results of the research are applied to a bulk-type medium as they are, it is difficult to obtain a desired pattern of transmitted shear waves. For this reason, it is necessary to design an apparatus and method capable of transmitting shear waves in a desired pattern to even a bulk-type medium.

DETAILED DESCRIPTION OF THE INVENTION

Technical Problem

The present invention provides an apparatus capable of transmitting shear waves in a desired pattern to a bulk-type medium and a method of transmitting shear waves by using the apparatus.

The present invention also provides a waveguide that aids in transmitting the shear waves of the desired pattern to the bulk-type medium in the above process.

Technical Solution

According to an aspect of the present invention, there is provided a waveguide including a vibrating portion which is vibrated by a vibrating unit and manufactured to have a plate shape, a transmitting portion which transmits shear waves generated by the vibrating unit to a bulk-type medium and is manufactured to have a plate shape thicker than the vibrating portion, and a connecting portion which contacts both the vibrating portion and the transmitting portion and has a thickness varying from a portion contacting the vibrating portion to a portion contacting the transmitting portion.

According to an aspect of the present invention, there is provided a vibrator for transmitting shear waves to a bulk-type medium, the vibrator including a vibrating unit which vibrates a waveguide to transmit shear waves along the waveguide, and the waveguide including a vibrating portion which is vibrated by the vibrating unit and manufactured to have a plate shape, a transmitting portion which transmits shear waves generated by the vibrating unit to a bulk-type medium and is manufactured to have a plate shape thicker than the vibrating portion, and a connecting portion which contacts both the vibrating portion and the transmitting portion and has a thickness varying from a portion contacting the vibrating portion to a portion contacting the transmitting portion.

Here, the vibrating portion may include a portion made of a ferromagnetic material, the vibrating unit may include an insulator which is disposed on the vibrating portion, meander coils which include a plurality of coil lines extending in a width direction of the vibrating portion on the insulator and are formed such that current flows in opposite directions along coil lines adjacent to each other, and a magnet which forms a magnetic field in the width direction of the vibrating portion, and when one or more meander coils selected from among the meander coils are supplied with current, portions of the vibrating portion corresponding to positions where the meander coils are disposed may be locally deformed, such that the shear waves are generated at the vibrating portion.

Here, the vibrating unit may include a mangetostrictive patch which is attached to a surface of the vibrating portion, an insulator disposed on the magnetostrictive patch, meander coils which include a plurality of coil lines extending in a width direction of the vibrating portion on the insulator and are formed such that current flows in opposite directions along coil lines adjacent to each other, and a magnet which forms a magnetic field in a width direction of the magnetostrictive patch, and when one or more meander coils selected from among the meander coils are supplied with current, portions of the magnetostrictive patch corresponding to positions where the meander coils are disposed may be locally deformed, such that the shear waves are generated at the vibrating portion.

Here, the vibrator may further include a wedge which is interposed between the waveguide and the bulk-type medium, and has a semi-cylindrical shape having a semi-circular cross section and a length corresponding to a width of the waveguide (width in an x-axis direction in FIG. 19), a contact surface at a lower end of the waveguide may be formed as a curved surface corresponding to a curved surface of the wedge, and the shear waves may be transmitted in a desired direction to the bulk-type medium when the contact surface of the waveguide is in contact with a desired position on the curved surface of the wedge.

Here, the wedge may further include a link connecting portion which extends from a lower rectangular surface of the semi-cylindrical shape downward toward the bulk-type medium, and a connecting link which is connected to both the link connecting portion and the waveguide and helps the waveguide to be maintained at a position on the wedge.

According to an aspect of the present invention, there is provided a method of transmitting shear waves to a bulk-type medium by using a waveguide including a vibrating portion vibrated by a vibrating unit and manufactured to have a plate shape, a transmitting portion transmitting shear waves generated by the vibrating unit to a bulk-type medium and manufactured to have a plate shape thicker than the vibrating portion, and a connecting portion contacting both the vibrating portion and the transmitting portion and having a thickness varying from a portion contacting the vibrating portion to a portion contacting the transmitting portion, the method including deciding a pattern and a frequency of the shear waves to be transmitted to the bulk-type medium (S1), deciding a thickness of the transmitting portion of the waveguide corresponding to the pattern decided in S1 (S2), deciding a thickness of a plate generating only a first mode of the shear waves at the decided frequency, and setting the decided thickness of the plate as a thickness of the vibrating portion (S3), and connecting the transmitting portion of the waveguide to the bulk-type medium, and transmitting the shear waves to the vibrating portion by using the vibrating unit (S4).

Here, the method may further include deciding a propagation direction of the shear waves to be transmitted to the bulk-type medium (S5), and installing a semi-cylindrical wedge between the transmitting portion and the bulk-type medium, contacting the transmitting portion of the waveguide with the semi-cylindrical wedge, and then disposing the waveguide in parallel to a direction in which the shear waves are to be transmitted (S6).

Advantageous Effects

According to the present invention, by using a waveguide, it is possible to block shear waves of higher-order modes, that is, second and higher modes, and enable transmission of shear waves of a first mode only.

According to the present invention, it is also possible to provide an apparatus and method capable of transmitting shear waves in a desired pattern and direction to a bulk-type medium by using a waveguide that transmits shear waves of a first mode only.

According to the present invention, when a target medium is a high-temperature medium or a medium in liquid or viscous fluid, it is also possible to transmit shear waves to the medium by using a long waveguide of the present invention.

Best Mode

Hereinafter, preferred embodiments of the present invention will be described in further detail with reference to the accompanying drawings.

Research results indicate that, when a waveguide is used, ultrasonic waves of several modes superpose each other, and thus it is difficult to control ultrasonic waves transmitted to a bulk-type medium in a uniform pattern. Here, a pattern of waves can be found in a graph showing a radiation pattern of the waves, that is, the shape of a line linking magnitudes of the waves transmitted at the same distance, and shows a propagation direction of the waves.

Figure 1:
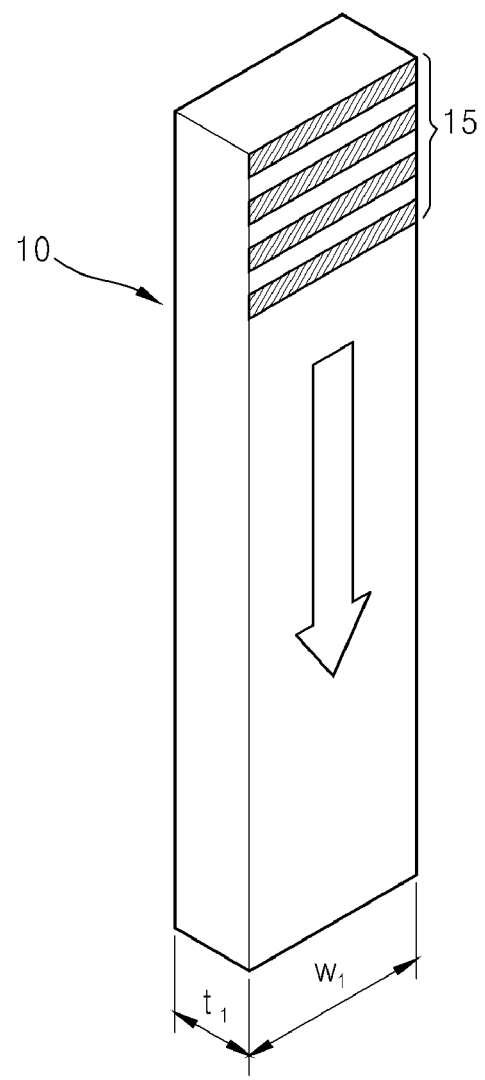
FIG. 1 is a perspective view generally showing a configuration of a planar waveguide of a comparative example to the present invention.

From simulation results of a case of using the following waveguide shown in FIG. 1, it is possible to clearly see that, when a waveguide is used, ultrasonic waves of several modes superpose each other, and thus it is difficult to control ultrasonic waves transmitted to a bulk-type medium in a uniform pattern.

FIG. 1 is a perspective view generally showing a configuration of a planar waveguide of a comparative example of the present invention, and FIGS. 2 to 5 are graphs of simulation results showing the form of propagation when shear waves are transmitted to a bulk-type medium by using the waveguide of FIG. 1.

Figure 2:
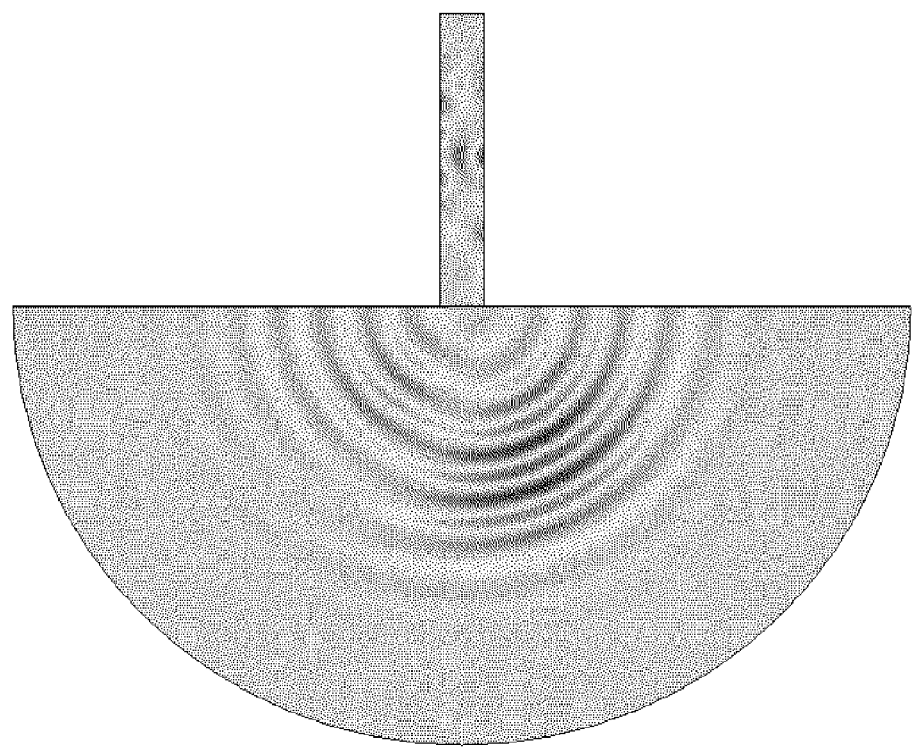
FIGS. 2 to 5 are graphs of simulation results showing the form of propagation when shear waves are transmitted to a bulk-type medium by using the waveguide of FIG. 1.
Figure 3:
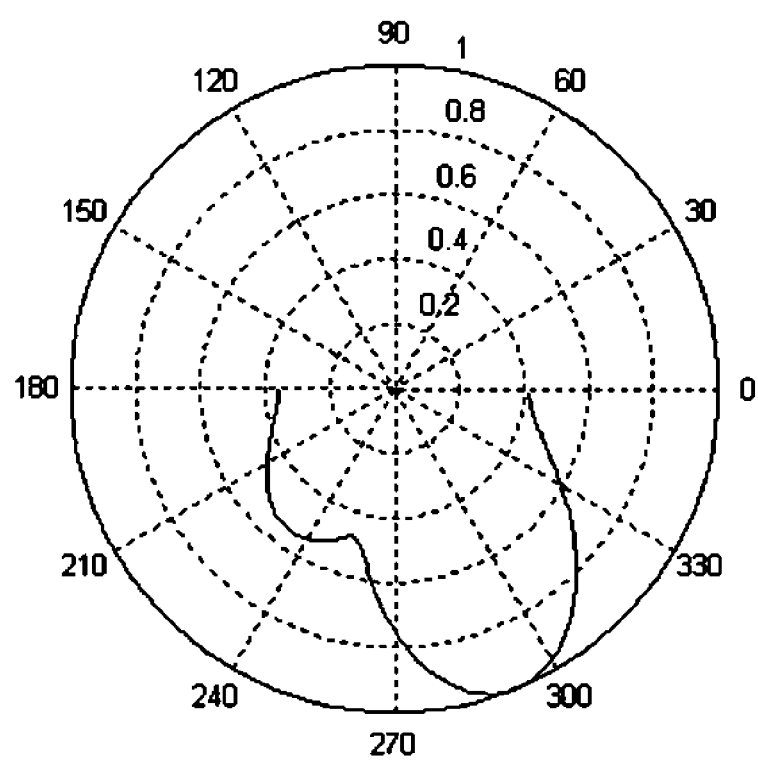
Figure 4:
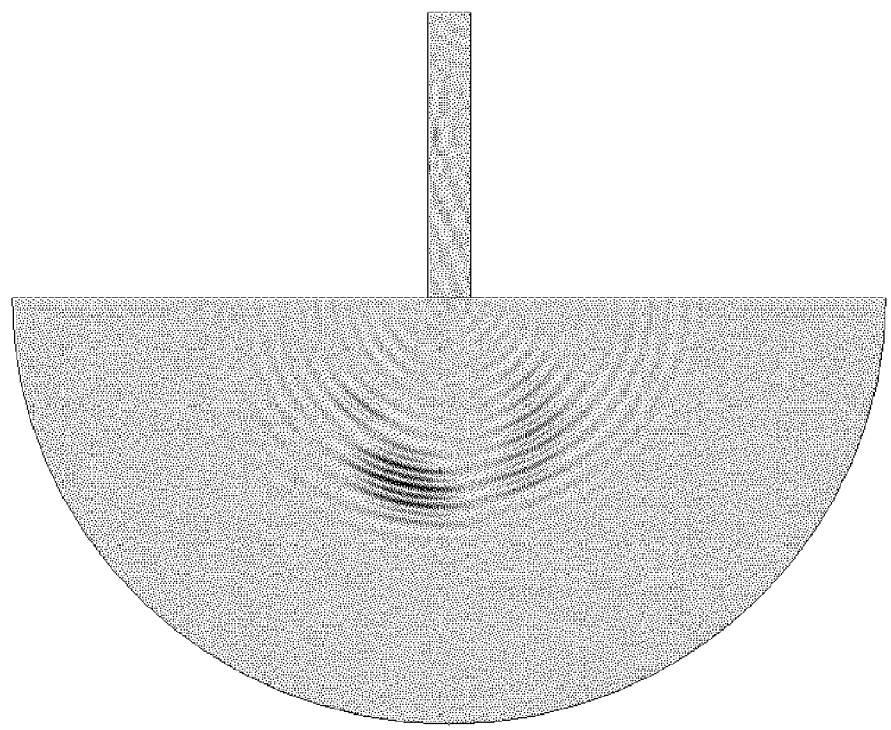
Figure 5:
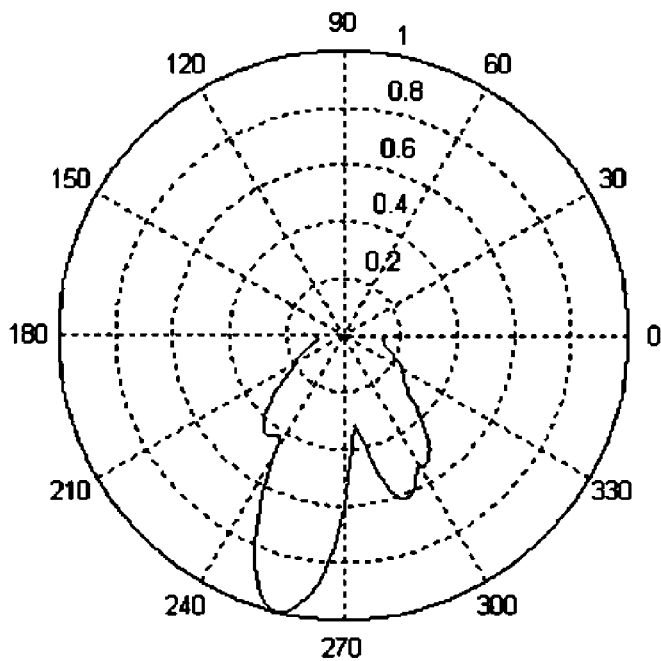

When the waveguide shown in FIG. 1 is used and a contact portion between the bulk-type medium and the waveguide has a thickness of 15 mm, shear waves are transmitted in a pattern of FIGS. 2 and 3 at 200 kHz. When the same waveguide vibrates at 500 kHz, shear waves are transmitted in a pattern shown in FIGS. 4 and 5. In other words, it is impossible to transmit shear waves in a specific direction and a uniform pattern.

Research results indicate that this is because shear waves of a first mode and higher-order modes, that is, second and higher modes, are transmitted while superposing each other. A reason why it is difficult to control a pattern of transmitted shear waves when a planar waveguide is used will be described below with reference to FIGS. 6 to 10.

Figure 6:
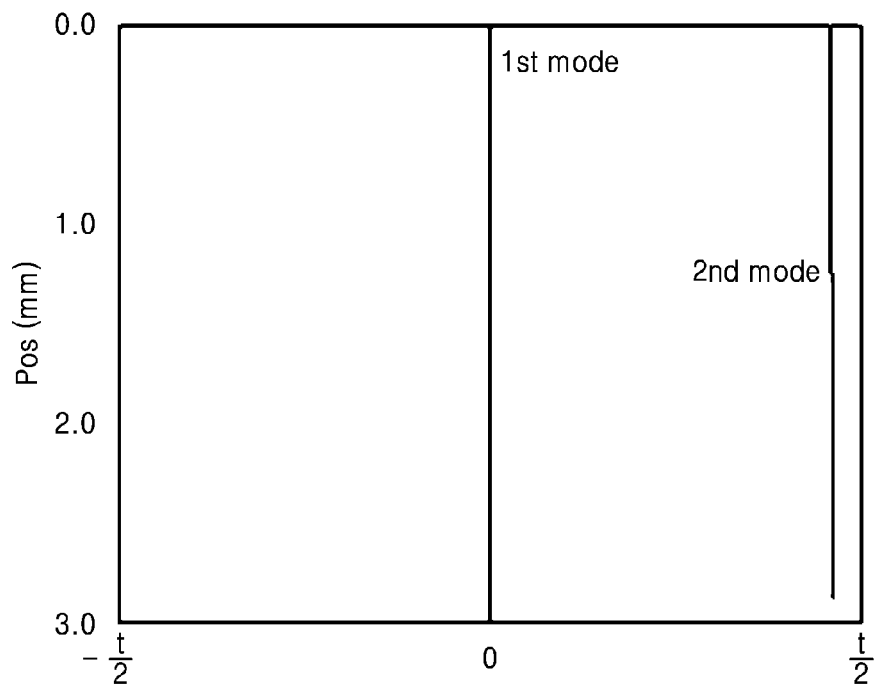
FIG. 6 is a phase graph showing a mode shape of a first mode when shear waves are transmitted to a bulk-type medium by using the waveguide of FIG. 1.
Figure 7:
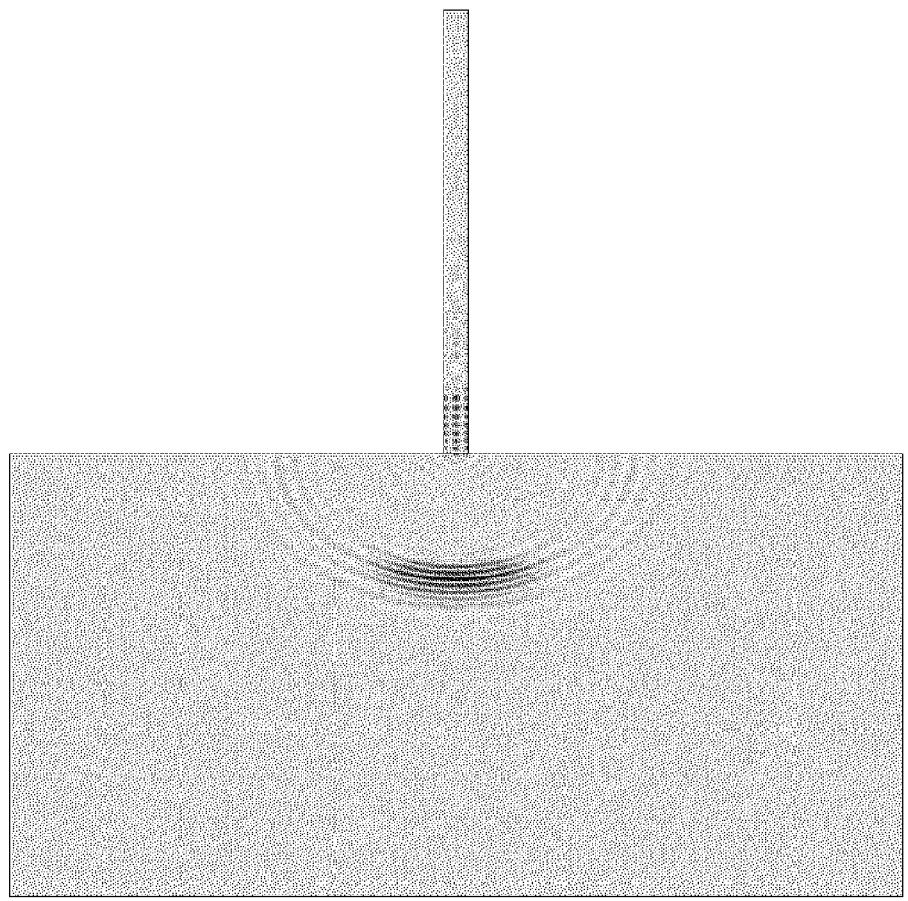
FIG. 7 is a graph showing the propagation form of waves when only a first mode is transmitted to a bulk-type medium by using the waveguide of FIG. 1.
Figure 8:
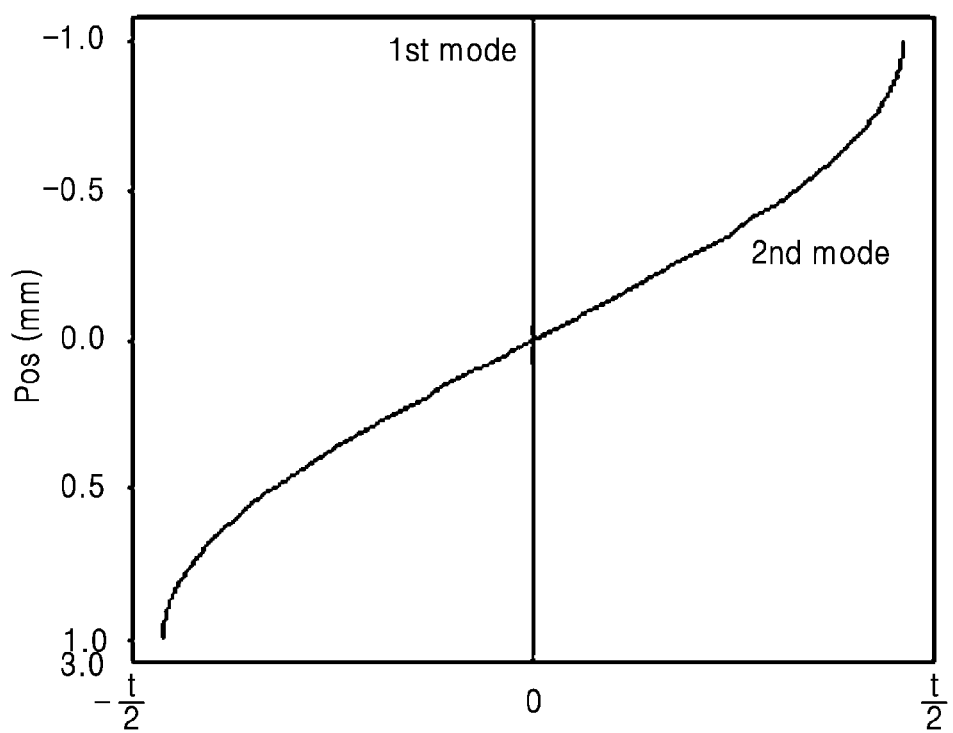
FIG. 8 is a phase graph showing a mode shape of a second mode when shear waves are transmitted to a bulk-type medium by using the waveguide of FIG. 1.
Figure 9:
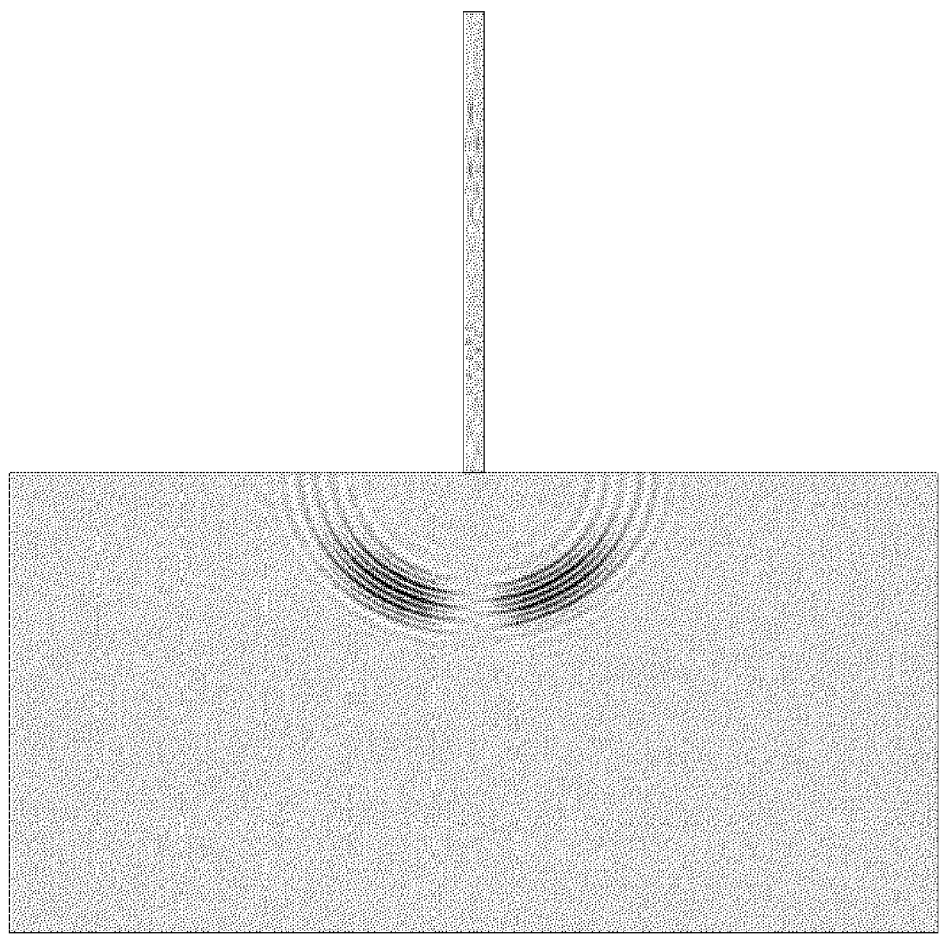
FIG. 9 is a graph showing the propagation form of waves when only a second mode is transmitted to a bulk-type medium by using the waveguide of FIG. 1.
Figure 10:
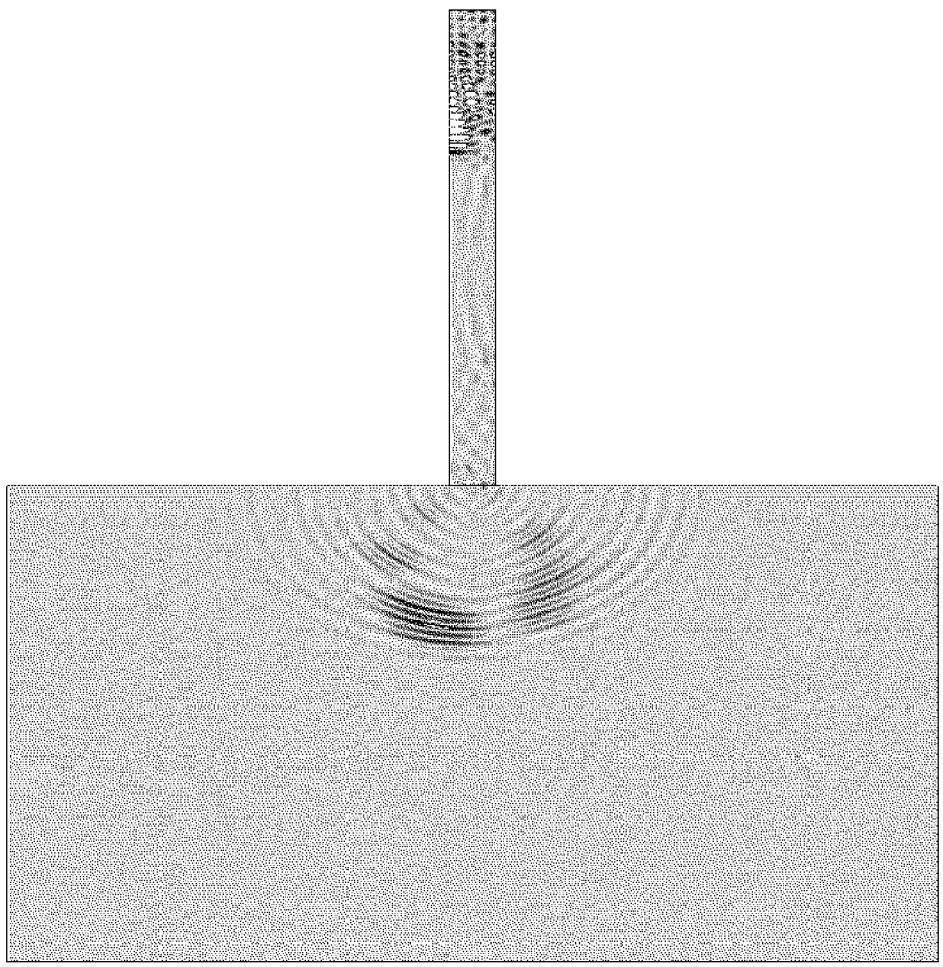
FIG. 10 is a graph showing the propagation form of waves when a first mode and a second mode are simultaneously transmitted to a bulk-type medium by using the waveguide of FIG. 1.

FIG. 6 is a phase graph showing a mode shape of a first mode, and FIG. 7 is a graph showing the propagation form of waves when only a first mode is transmitted. FIG. 8 is a phase graph showing a mode shape of a second mode, and FIG. 9 is a graph showing the propagation form of waves when only a second mode is transmitted. FIG. 10 is a graph showing the propagation form of waves when a first mode and a second mode are simultaneously transmitted.

When the first mode and the second mode are simultaneously transmitted, the first mode shown in FIG. 7 and the second mode shown in FIG. 9 superpose each other such that shear waves are transmitted in a distorted shape as shown in FIG. 10.

Figure 11:
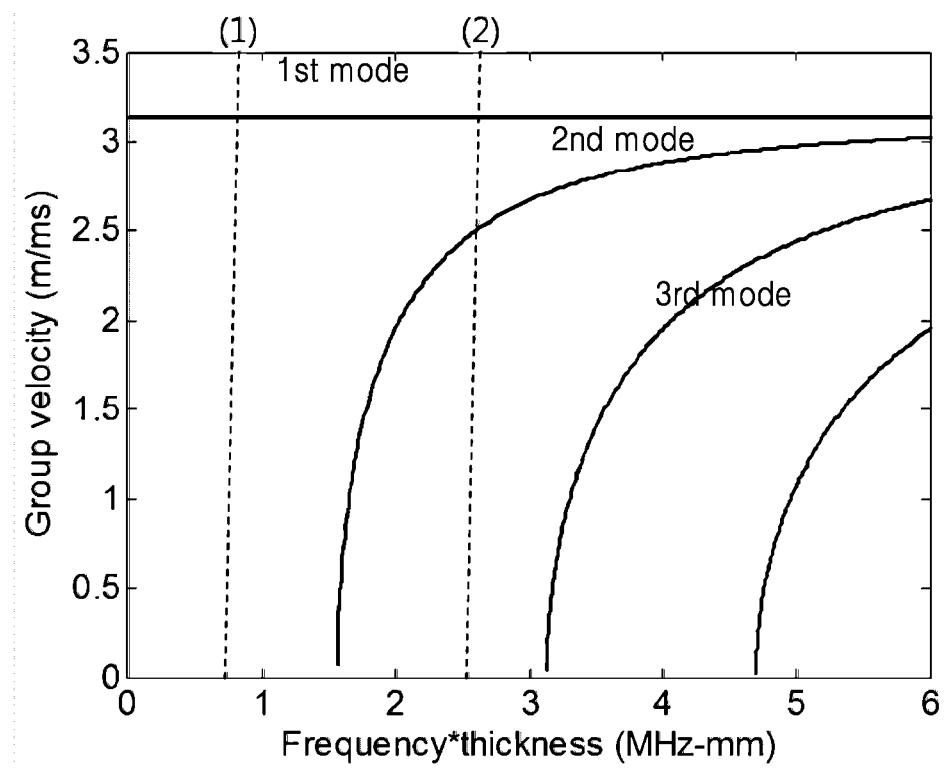
FIG. 11 shows shear-wave dispersion curves for an aluminum plate.

FIG. 11 is a graph showing a case where higher-order modes, that is, second and higher order modes, are generated.

The graph of FIG. 11 shows shear-wave dispersion curves for a planar aluminum waveguide having a uniform thickness (see FIG. 1), in which the horizontal axis denotes a product of a frequency and the thickness of a plate, and the vertical axis denotes the velocity of shear waves. Among lines in the graph, a horizontally-extending straight line denotes a first mode, and curves denote higher-order modes, that is, second and higher order modes, sequentially from left to right.

As shown in FIG. 11, when the product of a frequency and the thickness is small ((1) of FIG. 11), shear waves of the first mode are transmitted at all times. However, when the product of a frequency and the thickness increases ((2) of FIG. 11), shear waves of a second mode are generated.

Consequently, by setting the product of a frequency and the thickness to be in a low range in which only the first mode is generated, only the first mode can be transmitted.

Meanwhile, when an overall waveguide is formed to have a small thickness, only shear waves of the first mode can be transmitted in the longitudinal direction of the waveguide. However, a pattern of transmitted shear waves is set to one pattern, and a pattern of shear waves cannot be obtained in a desired shape.

Research results indicate that a pattern of transmitted shear waves directly relates to the thickness of a portion of a waveguide contacting a bulk-type medium. In other words, when the thickness of the portion of the waveguide contacting the bulk-type medium is large, in a narrow area, shear waves having a higher magnitude that is proportional to the thickness than in the surrounding area are transmitted in a direction parallel to the longitudinal direction of the waveguide. Also, as the thickness of the portion of the waveguide contacting the bulk-type medium decreases, the difference between the magnitude of shear waves transmitted in the direction parallel to the longitudinal direction of the waveguide and the magnitude of shear waves in the surrounding area is reduced.

Figure 12:
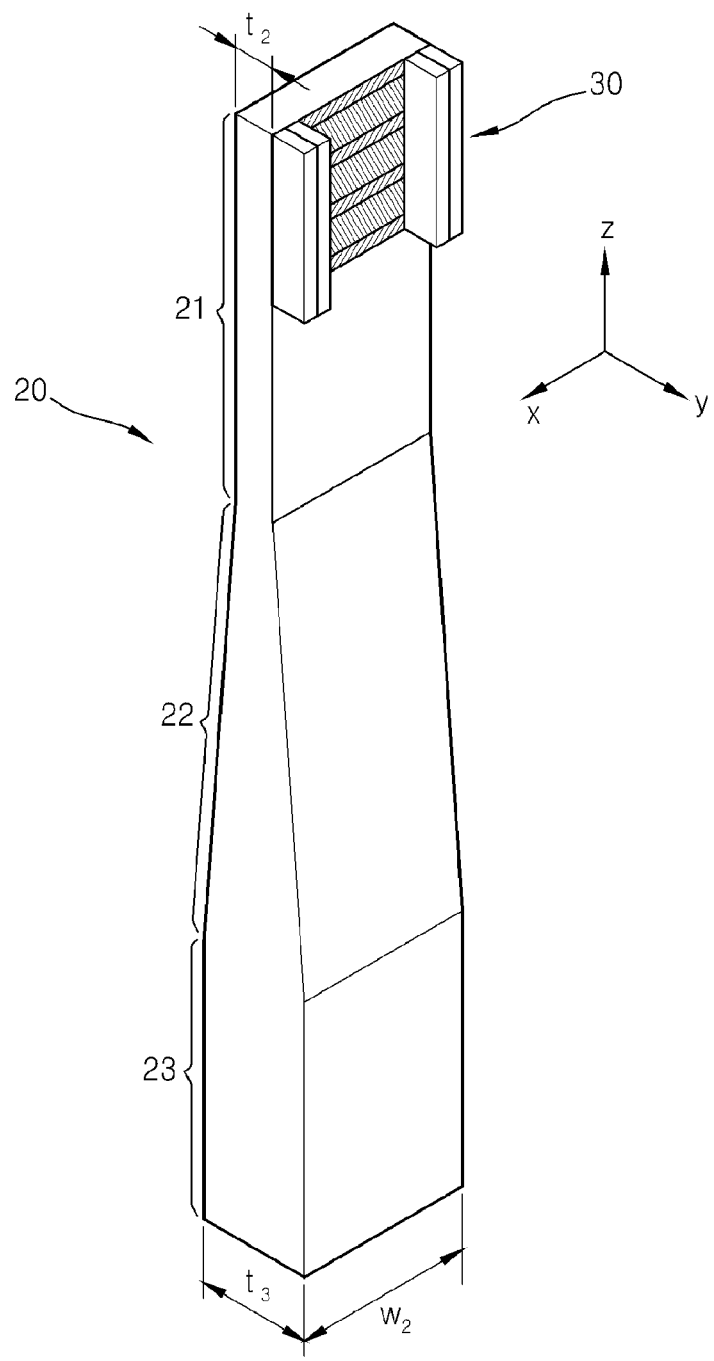
FIG. 12 is a perspective view showing a configuration of a waveguide for transmitting shear waves to a bulk-type medium according to Embodiment 1 of the present invention.

Accordingly, a waveguide as shown in FIG. 12 has been developed in the present invention.

FIG. 12 is a perspective view showing a configuration of a waveguide for transmitting shear waves to a bulk-type medium according to Embodiment 1 of the present invention.

As shown in FIG. 12, a waveguide 20 according to the present invention includes a vibrating portion 21 that is vibrated by a vibrating unit and manufactured to have a plate shape, a transmitting portion 23 that transmits shear waves generated by the vibrating unit and is manufactured to have a plate shape thicker than the vibrating portion 21, and a connecting portion 22 that contacts both the vibrating portion 21 and the transmitting portion 23 and has a thickness varying from a portion contacting the vibrating portion 21 to a portion contacting the transmitting portion 23.

When the waveguide 20 having such a shape is used, the thicknesses of the vibrating portion 21 and the transmitting portion 23 are decided as follows. That is, the thickness of the vibrating portion 21 is decided such that a product of the frequency of a transmitted shear wave and the thickness of the vibrating portion 21 becomes equal to or less than a product of a cut-off frequency of a second mode and the thickness of the vibrating portion 21 in a shear-wave dispersion curve for a plate, and the thickness of the transmitting portion 23 is decided so that shear waves of a desired pattern can be transmitted. The thickness of the transmitting portion 23 is selected to be larger than that of the vibrating portion 21 because there is no need to use a waveguide of the present invention when the thickness of the transmitting portion 23 is equal to or less than that of the vibrating portion 21.

When the waveguide 20 having a size decided in this way is used, it is possible to transmit shear waves to a bulk-type medium in a desired pattern while solving a problem that it is difficult to control a pattern of shear waves in which the shear waves of a first mode and higher-order modes, that is, second and higher order modes, are transmitted while superposing each other.

Meanwhile, the connecting portion 22 can be formed to have a tapering cross-sectional shape whose thickness uniformly varies from the thickness of the vibrating portion 21 to the thickness of the transmitting portion 23, but is not limited to the tapering shape. In other words, the only function of the connecting portion 22 is to transmit shear waves generated by the vibrating portion 21 to the transmitting portion 23, and thus the portion contacting the vibrating portion 21 or the transmitting portion 23 may have a different thickness from the vibrating portion 21 or the transmitting portion 23. In addition, the thickness may not only gradually increase from the vibrating portion 21 to the transmitting portion 23, but may also be larger than that of the vibrating portion 21 or the transmitting portion 23 in the middle of the connecting portion 22. However, in the case of the tapering shape shown in the drawing, little distortion occurs in transmitted shear waves due to reflection in the connecting portion 22, and the waveguide 20 may be easily manufactured.

Meanwhile, a change in the pattern of shear waves according to the thickness of a waveguide can be checked from the following simulation result graphs.

Figure 13:
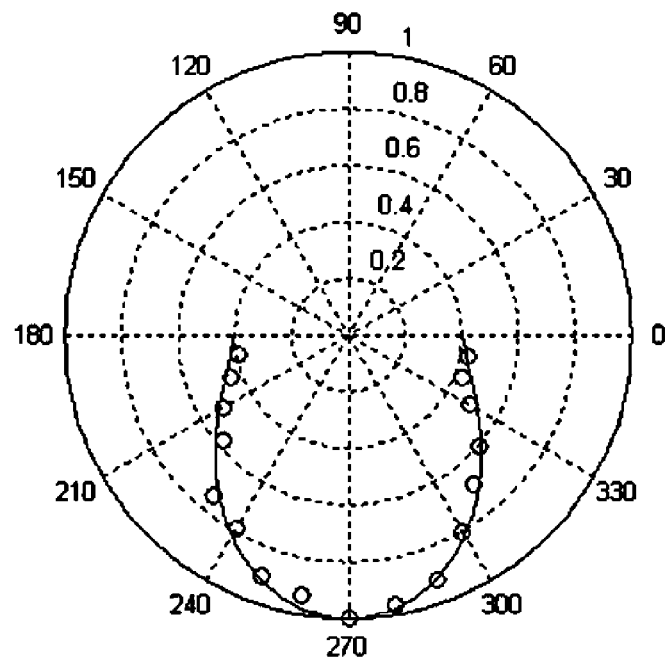
FIGS. 13 to 15 are graphs showing wave patterns when the waveguide of the present invention vibrates at 200 kHz while a thickness t3 of a transmitting portion of the waveguide changes to 10 mm, 15 mm, and 25 mm.
Figure 14:
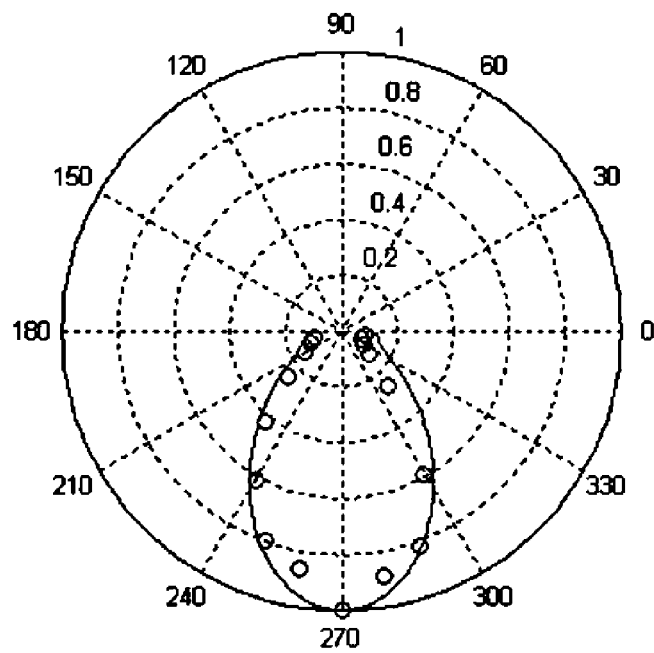
Figure 15:
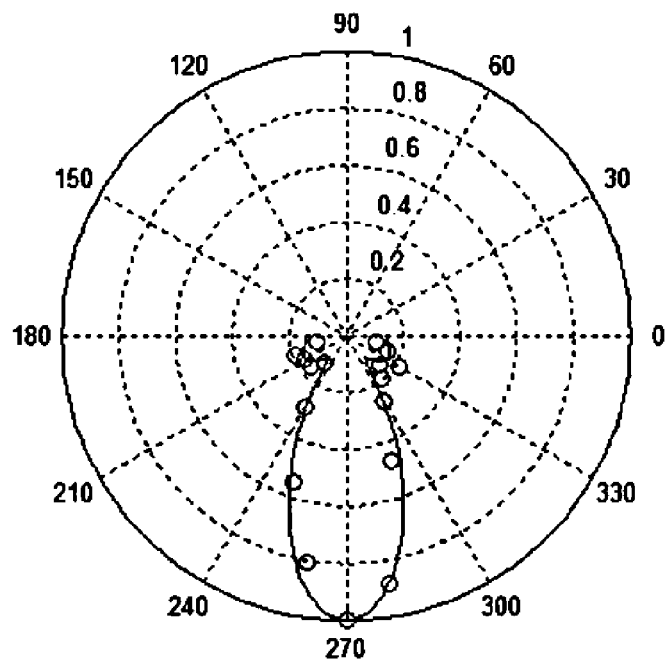
Figure 16:
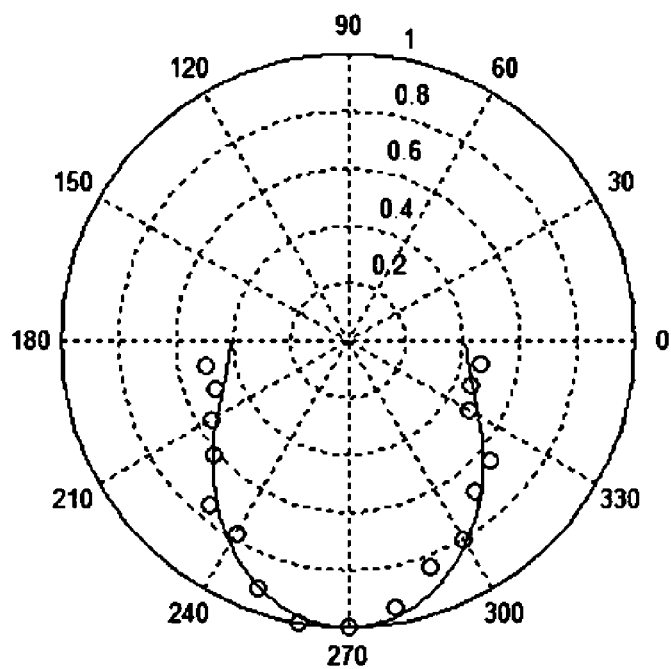
FIGS. 16 to 18 are graphs showing wave patterns when the waveguide of the present invention vibrates at 500 kHz while the thickness t3 of the transmitting portion of the waveguide changes to 4 mm, 6 mm, and 10 mm.
Figure 17:
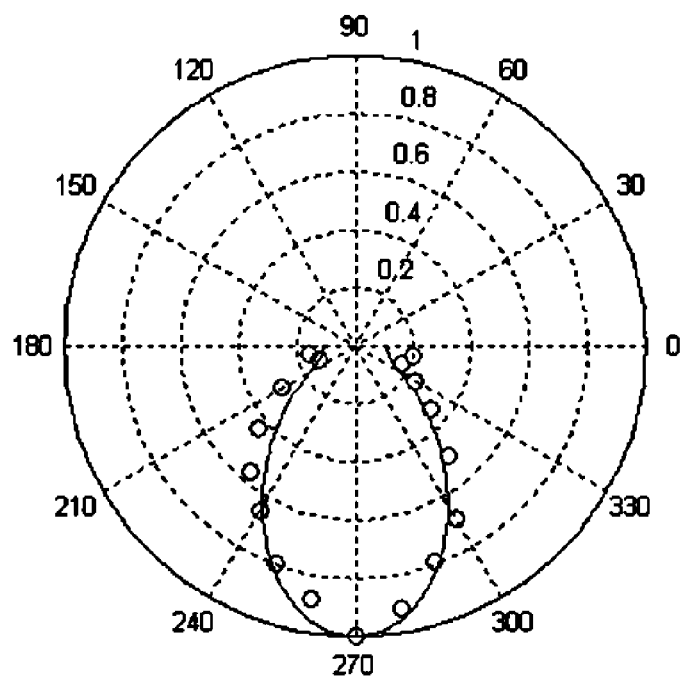
Figure 18:
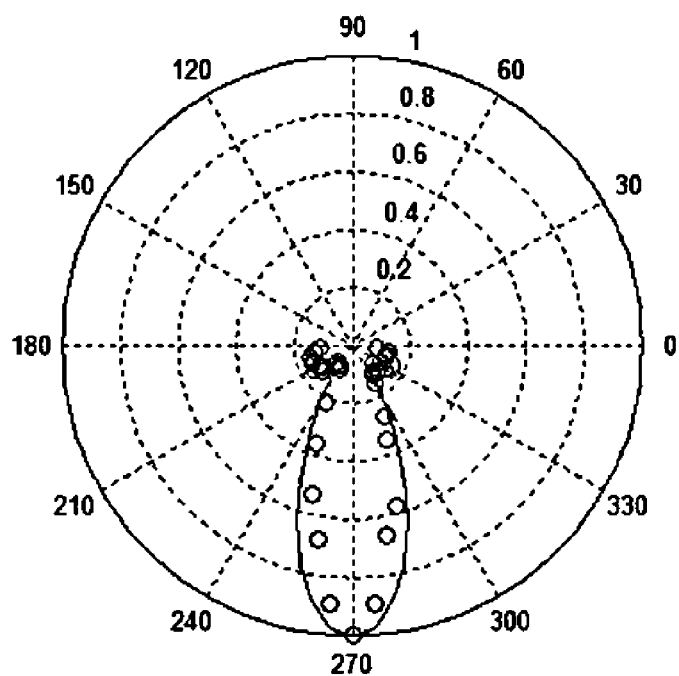

FIGS. 13 to 15 are graphs showing wave patterns when the waveguide 20 of the present invention is used and vibrates at 200 kHz while a thickness t3 of the transmitting portion 23 of the waveguide 20 changes to 10 mm, 15 mm, and 25 mm, and FIGS. 16 to 18 are graphs showing wave patterns when the waveguide 20 of the present invention vibrates at 500 kHz while the thickness t3 of the transmitting portion 23 of the waveguide changes to 4 mm, 6 mm, and 10 mm. In FIGS. 13 to 18, solid lines denote simulation analysis results, and small circles denote experimental results.

As shown in FIGS. 13 to 18, it is possible to determine that a wave pattern changes in a manner where the larger the thickness of the transmitting portion 23 of the waveguide 20 contacting a medium, the smaller area shear waves are concentrated and transmitted in, and as the thickness of the transmitting portion 23 of the waveguide 20 decreases, the difference between the magnitude of transmitted shear waves and the magnitude of waves in the surrounding area is reduced.

Mode of the Invention

Hereinafter, a vibrator using the above-described waveguide 20 will be described.

The vibrator according to the present invention is a vibrator that transmits shear waves to a bulk-type medium, and includes a vibrating unit 30 that vibrates the waveguide 20 to transmit shear waves along the waveguide 20, a vibrating portion 21 that is vibrated by the vibrating unit 30 and manufactured to have a plate shape, and the waveguide 20 that transmits the shear waves generated by the vibrating unit 30 to a bulk-type medium.

The waveguide is the same as waveguide 20 described above. However, to prevent ultrasonic reflection in the waveguide, a sound-absorbing material or a backing material may be additionally attached to an end (rear end of the vibrating portion) of the waveguide. Also, a transmitting material or a matching material that facilitates transmission of ultrasonic waves to the bulk-type medium may be additionally interposed between the waveguide and the bulk-type medium.

As the vibrating unit 30, various forms of plate vibrators can be used. For example, a magnetostrictive transducer, an electromagnetoacoustic transducer (EMAT), a transducer using a piezoelectric device, etc. can be used.

Among them, it is preferable to use the magnetostrictive transducer that enables generation of strong shear waves by superposition, and a configuration of the vibrating portion 21 will be briefly described with reference to FIG. 19.

Figure 19:
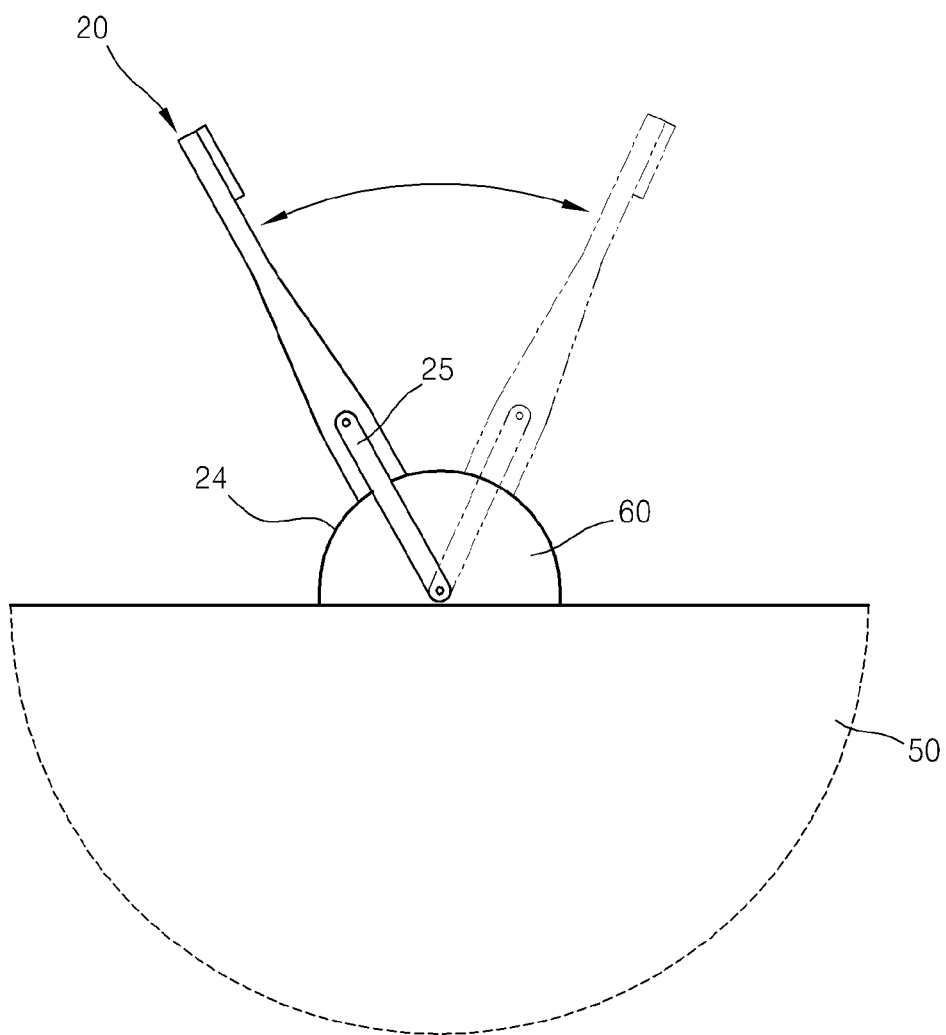
FIG. 19 is a lateral cross-sectional view of a vibrating unit disposed in a vibrating portion in the form of a magnetostrictive transducer that can be used in a shear-wave transmitting apparatus according to the present invention.

FIG. 19 shows the vibrating unit 30 in the form of a magnetostrictive transducer that can be used in a shear-wave transmitting apparatus according to the present invention, disposed in the vibrating portion 21.

As shown in FIG. 19, the vibrating unit 30 can include a magnetostrictive patch 201, an insulator 203, meander coils 204, and magnets 206.

The magnetostrictive patch 201 is attached to a surface of the vibrating portion 21, and is formed of a magnetic material, preferably, a ferromagnetic material such as iron (Fe), nickel (Ni), and cobalt (Co) or an alloy thereof, or a material with high magnetostriction.

The meander coils 204 include a plurality of coil lines A, B, C, etc. extending in the width direction of the vibrating portion 21, and is formed such that current flows in opposite directions along coil lines adjacent to each other.

The insulator 203 is interposed between the magnetostrictive patch 201 and the meander coils 204, functioning to electrically insulate the meander coils 204 and the magnetostrictive patch 201.

The magnets 206 are disposed such that different poles face each other at both ends of the width direction of the magnetostrictive patch 201 to form a magnetic field in the width direction.

When current is supplied to the meander coils 204 in such a configuration, portions of the magnetostrictive patch 201 corresponding to positions where the coil lines A, B, C, etc. are respectively disposed, are locally deformed due to the magnetostriction effect, such that shear waves are generated at the magnetostrictive patch 201 and the vibrating portion 21 to which the magnetostrictive patch 201 is attached.

Alternatively, when the vibrating portion 21 itself is formed of a same type of ferromagnetic material as the magnetostrictive transducer, the magnetostrictive patch 201 can be omitted. In this case, the insulator 203, the meander coils 204, and the magnets 206 are configured in substantially the same way as described above.

In addition, when a distance d between the coil lines A, B, C, etc. constituting the meander coils 204 is adjusted to be half the wavelength of the generated shear waves, the shear waves generated at the positions where the coil lines A, B, C, etc. are disposed superpose each other and constructively interfere with each other such that shear waves having greater magnitudes can be transmitted.

A method of transmitting shear waves to a bulk-type medium according to the present invention will be described below.

In the method of transmitting shear waves to a bulk-type medium according to the present invention, the waveguide 20 having the same shape as described above, in which the vibrating portion 21 has a small thickness, the transmitting portion 23 has a large thickness, and the connecting portion 22 connecting the vibrating portion 21 and the transmitting portion 23 is prepared, is used.

In the method of the present invention, first, a pattern and frequency of shear waves to be transmitted to a bulk-type medium are decided. Then, the thickness of the transmitting portion 23 of the waveguide 20 corresponding to the determined pattern is decided. Subsequently, the thickness of a plate that generates only a first mode of the shear waves at the determined frequency is decided and determined as the thickness of the vibrating portion 21.

After the size of the waveguide 20 is decided in this way, the transmitting portion 23 of the waveguide 20 is connected to the bulk-type medium, and the shear waves are transmitted to the vibrating portion 21 by using the vibrating unit 30.

Figure 20:
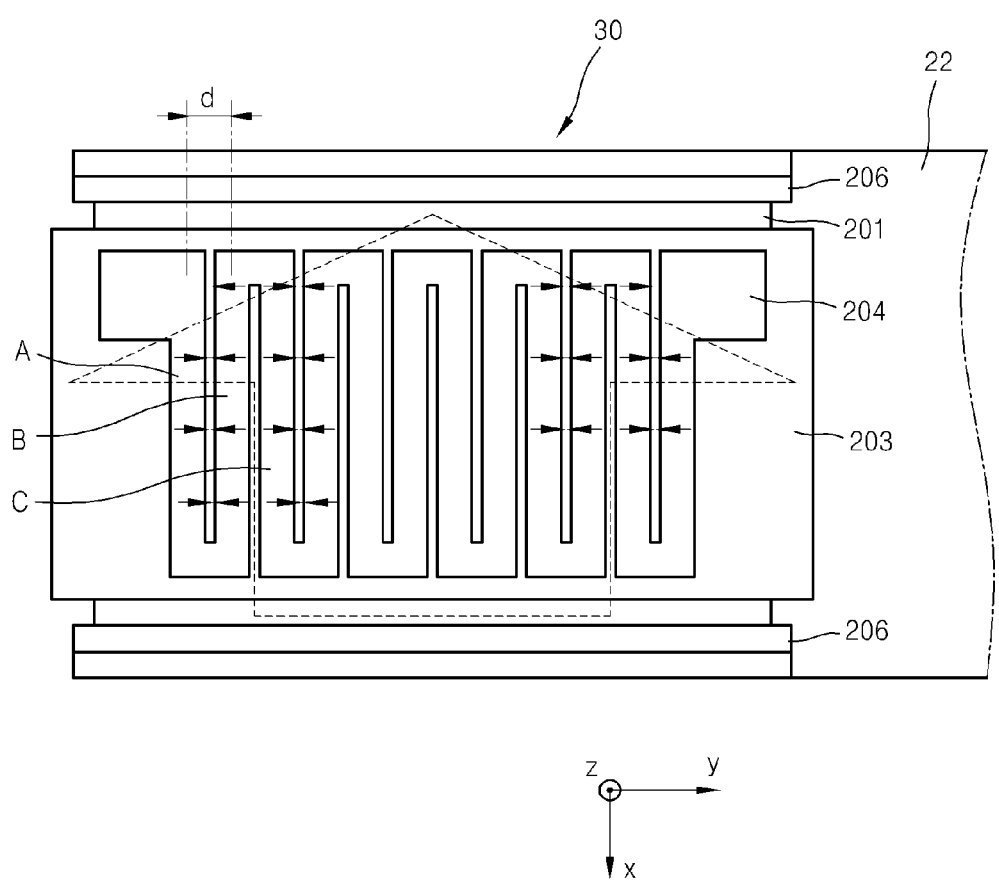
FIG. 20 is a lateral cross-sectional view showing a configuration of an embodiment of a vibrator that transmits shear waves in a desired direction to a bulk-type medium of the present invention.

When a surface of the bulk-type medium is planar, a vibrator as shown in FIG. 20 can be used to transmit shear waves in a direction other than the longitudinal direction of the waveguide 20 instead of disposing the waveguide 20 vertically on the surface and then transmitting shear waves in the length direction of the waveguide 20.

FIG. 20 is a lateral cross-sectional view showing a configuration of an embodiment of a vibrator that transmits shear waves in a desired direction to a bulk-type medium of the present invention.

As shown in FIG. 20, the vibrator of the present invention includes the waveguide shown in FIG. 12, a vibrating unit installed in the vibrating portion of the waveguide, and a wedge 60 interposed between the waveguide and a bulk-type medium 50 that is a vibration target.

The wedge 60 has a semicircular cross sectional shape, and is manufactured to have a semi-cylindrical shape having a length corresponding to the width of the waveguide (width in the x-axis direction in FIG. 20).

Configurations of the waveguide and the vibrating unit are the same as described above. However, a contact surface 24 at the lower end of the waveguide is preferably formed as a curved concave surface corresponding to the curved surface of the wedge 60.

When shear waves are transmitted by using the vibrator having such a configuration with the contact surface of the waveguide contacting a desired position on the curved surface of the wedge 60, the shear waves can be transmitted in a direction parallel to the longitudinal direction of the waveguide to the bulk-type medium 50.

Meanwhile, the vibrator that transmits shear waves in a desired direction to the bulk-type medium 50 according to the present invention may further include the following components shown in FIG. 20.

That is, the wedge 60 may further include a link connecting portion 60a that extends from the lower rectangular surface of the semi-cylindrical shape downward toward the bulk-type medium 50, and a connecting link 25 that is connected to the link connecting portion 60a and the waveguide and maintains the waveguide at a position on the wedge 60, thereby providing convenience of use.

FIGS. 21 to 26 show graphs of radiation patterns showing results of shear waves being transmitted in desired directions to a bulk-type medium when the waves are incident on the bulk medium through a diagonally-installed waveguide.

Figure 21:
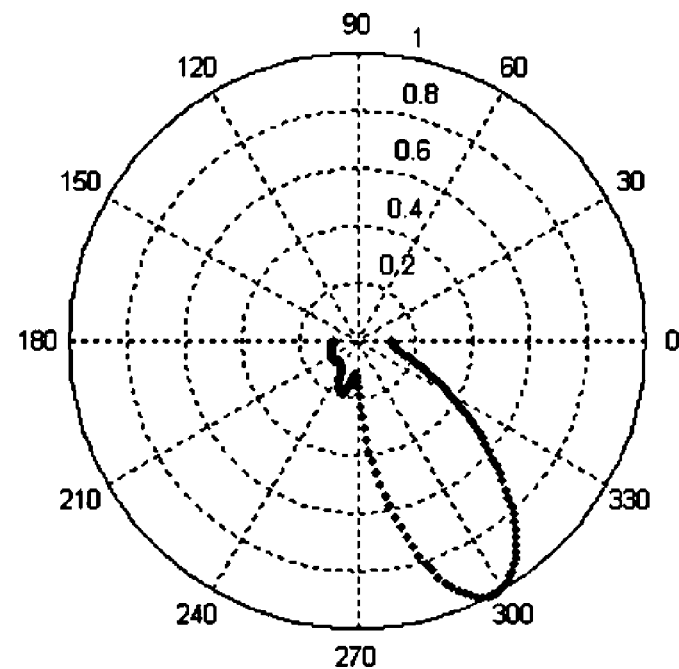
FIGS. 21 to 23 are graphs showing radiation patterns when shear waves are transmitted to a bulk-type medium at a frequency of 200 kHz while an angle changes to 30 degrees, 45 degrees, and 60 degrees.
Figure 22:
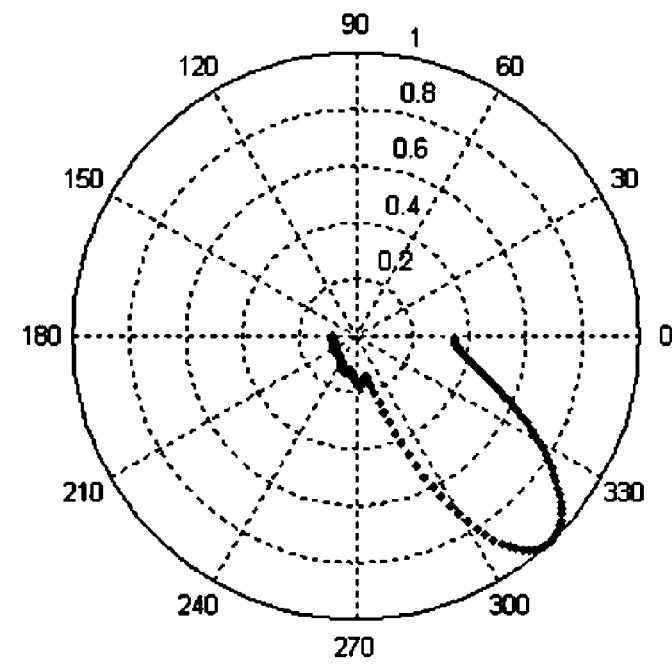
Figure 23:
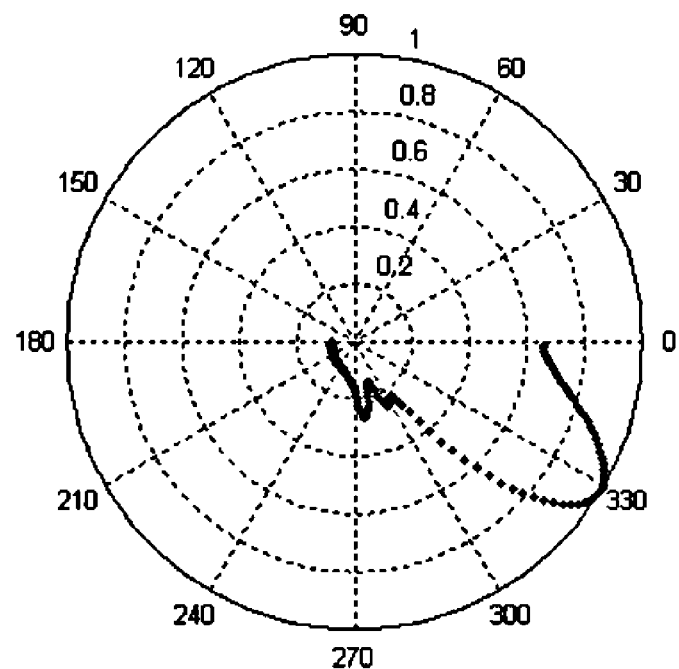
Figure 24:
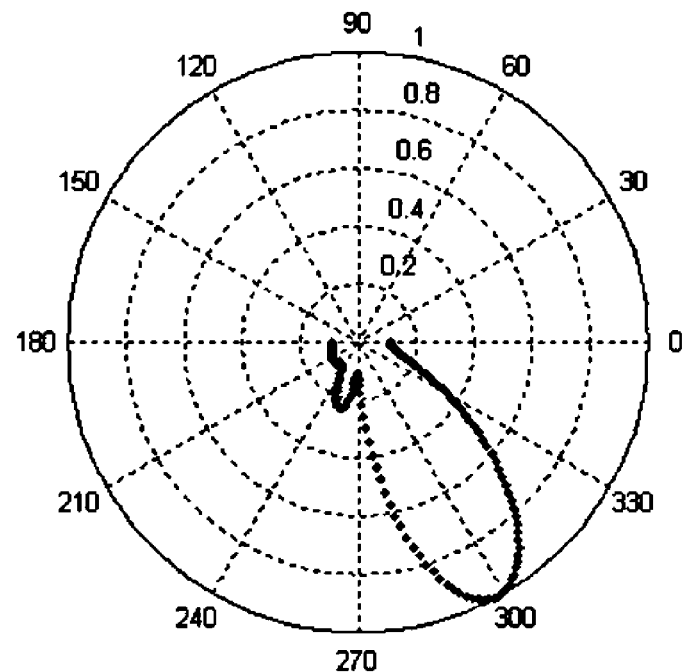
FIGS. 24 to 26 are graphs showing radiation patterns when shear waves are transmitted to a bulk-type medium at a frequency of 500 kHz while an angle changes to 30 degrees, 45 degrees, and 60 degrees.
Figure 25:
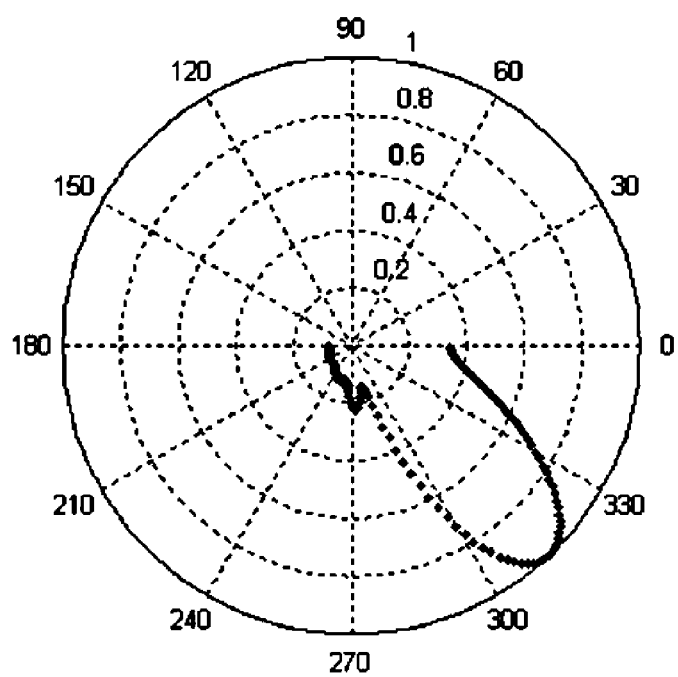
Figure 26:
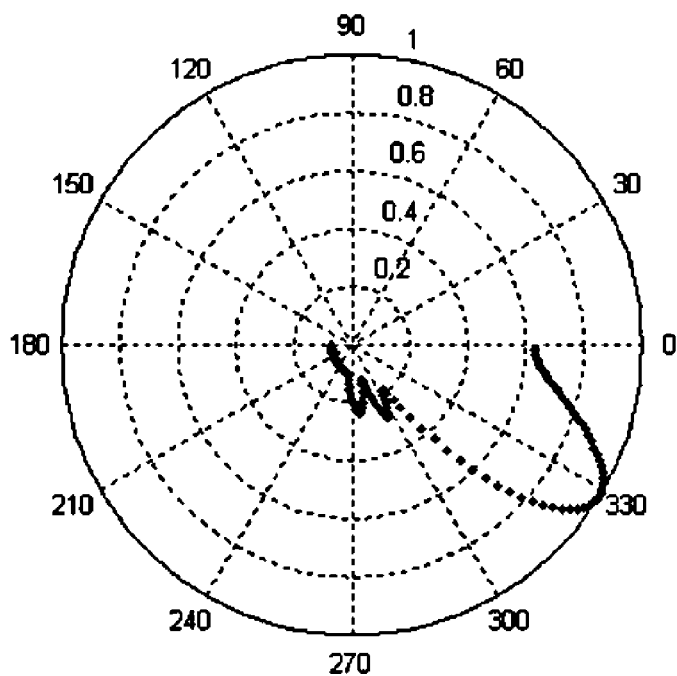

FIGS. 21 to 23 are graphs showing radiation patterns when shear waves are transmitted to a bulk-type medium at a frequency of 200 kHz while an angle changes to 30 degrees, 45 degrees, and 60 degrees, and FIGS. 24 to 26 are graphs showing radiation patterns when shear waves are transmitted to a bulk-type medium at a frequency of 500 kHz while an angle changes to 30 degrees, 45 degrees, and 60 degrees. As can be seen from the graphs, it is possible to control the direction of a radiation pattern by using a wedge.

Figure 27:
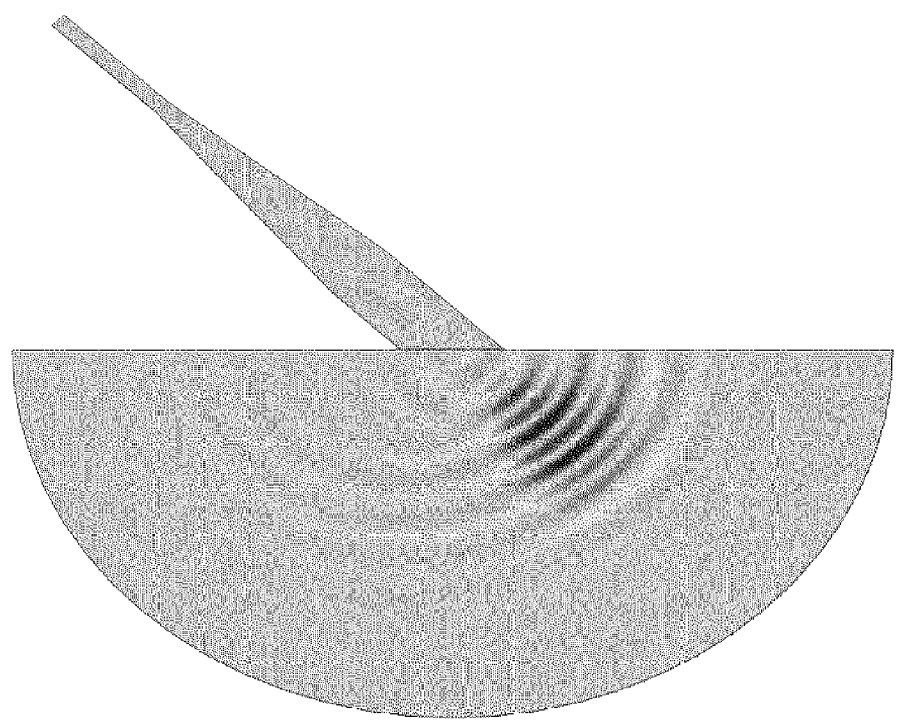
FIG. 27 is a diagram showing shear waves that are transmitted in a diagonal direction to a bulk-type medium by using a waveguide according to another embodiment of the present invention.

FIG. 27 is a diagram showing shear waves that are transmitted in a diagonal direction to a bulk-type medium by using a waveguide according to Embodiment 2 of the present invention.

As shown in FIG. 27, the waveguide according to Embodiment 2 of the present invention is different from the waveguide of Embodiment 1 described above and the waveguide of the modified example in that an inclined surface is formed at an end of the transmitting portion. The inclined surface is formed at the end of the transmitting portion such that the propagation direction of shear waves is set according to the angle of the inclined surface.

According to the waveguide of Embodiment 1, a surface of a medium is perpendicular to the central axis of the longitudinal direction of the waveguide. To overcome the limitation that the propagation direction of shear waves is only a direction perpendicular to the medium surface, Embodiment 1 is used with a wedge, and a curved surface corresponding to the curvature of a wedge surface is formed at an end of a transmitting portion. Use of a wedge has been described above with reference to FIG. 20.

In Embodiment 2, the shear wave propagation direction of the waveguide is set to a specific diagonal direction. According to a purpose, it may be preferable to transmit shear waves in a specific diagonal direction. In Embodiment 2 also, the propagation direction of shear waves is the longitudinal direction of the waveguide. Shear waves are transmitted in a diagonal direction, which corresponds to an acute angle between the central axis parallel to the longitudinal direction of the waveguide and a surface of a medium, with respect to the medium surface.

Meanwhile, in the description of the present invention, no particular mention has been made of widths w1 and w2 of waveguides. However, since shapes of a plate, in which the widths w1 and w2 are much larger (at least three times larger) than thicknesses t1, t2, and t3, are taken into consideration, widths of various sizes can be selected and do not limit the scope of the present invention.

In addition, in the description of the present invention, only a case where a cross section taken in a direction perpendicular to the longitudinal direction of a waveguide is a rectangle has been included. However, not only in the case of a rectangle but also in the cases of a square, a circle, and an oval, it is possible to block shear waves of higher-order modes, that is, second and higher order modes, and enable transmission of shear waves of a first mode. Also, by using a waveguide that transmits shear waves of the first mode, it is possible to transmit shear waves in a desired pattern and direction to a bulk-type medium. However, when the cross section has a rectangular or square shape, most shear waves of higher-order modes are blocked, and shear waves are exactly transmitted in a desired pattern and direction.

Although the present invention has been described with reference to the embodiments depicted in the drawings, it is just an example, and it should be understood by those of ordinary skill in the art that various modifications and equivalents can be made thereto. Therefore, the true technical scope of the present invention should be defined by the technical spirit of the appended claims.

The invention claimed is:

1. A waveguide comprising:
a vibrating portion which has a plate shape, a width w2 and a thickness t2, and is vibrated by a vibrating unit;
a transmitting portion which transmits shear waves generated by the vibrating unit to a bulk-type medium, and has a plate shape, a width w2 and a thickness t3 that is thicker than the thickness t2 of the vibrating portion;
a connecting portion which contacts both the vibrating portion and the transmitting portion and has a thickness varying from a portion contacting the vibrating portion to a portion contacting the transmitting portion; and
a vibrating unit which generates a shear wave in the vibration portion in a direction parallel to the plane of the vibration portion,
wherein the width w2 is larger than the thickness t2 of the vibrating portion and the thickness t3 of the transmitting portion.

2. The waveguide of claim 1, wherein the transmitting portion is installed to contact the bulk-type medium while being used, and
an inclined surface inclined with respect to a longitudinal direction of the waveguide is formed at an end of the transmitting portion contacting the bulk-type medium.

3. A vibrator for transmitting shear waves to a bulk-type medium, the vibrator comprising:
a vibrating unit which vibrates a waveguide to transmit shear waves along the waveguide; and
the waveguide comprising a vibrating portion which has a plate shape, a width w2 and a thickness t2, and is vibrated by a vibrating unit; a transmitting portion which transmits shear waves generated by the vibrating unit to a bulk-type medium, and has a plate shape, a width w2 and a thickness t3 that is thicker than the thickness t2 of the vibrating portion; a connecting portion which contacts both the vibrating portion and the transmitting portion and has a thickness varying from a portion contacting the vibrating portion to a portion contacting the transmitting portion; and a vibrating unit which generates a shear wave in the vibration portion in a direction parallel to the plane of the vibration portion, wherein the width w2 is larger than the thickness t2 of the vibrating portion and the thickness t3 of the transmitting portion.

4. The vibrator of claim 3, wherein the vibrating portion comprises a portion made of a ferromagnetic material,
the vibrating unit comprises:
an insulator which is disposed on the vibrating portion;
meander coils which comprise a plurality of coil lines extending in a width direction of the vibrating portion on the insulator, and are formed such that current flows in opposite directions along coil lines adjacent to each other; and
a magnet which forms a magnetic field in the width direction of the vibrating portion, and
when one or more meander coils selected from among the meander coils are supplied with current, portions of the vibrating portion corresponding to positions where the meander coils are disposed are locally deformed, such that the shear waves are generated at the vibrating portion.

5. The vibrator of any one of claim 4, further comprising a wedge which is interposed between the waveguide and the bulk-type medium, and has a semi-cylindrical shape having a semicircular cross section and a length corresponding to a width of the waveguide that corresponds to the width direction of the vibrating portion,
wherein a contact surface at a lower end of the waveguide is formed as a curved surface corresponding to a curved surface of the wedge, and the shear waves are transmitted in a desired direction to the bulk-type medium when the contact surface of the waveguide is in contact with a desired position on the curved surface of the wedge.

6. The vibrator of claim 3, wherein the vibrating unit comprises:
a mangetostrictive patch which is attached to a surface of the vibrating portion;
an insulator disposed on the magnetostrictive patch;
meander coils which comprise a plurality of coil lines extending in a width direction of the vibrating portion on the insulator, and are formed such that current flows in opposite directions along coil lines adjacent to each other; and
a magnet which forms a magnetic field in a width direction of the magnetostrictive patch, and
when one or more meander coils selected from among the meander coils are supplied with current, portions of the magnetostrictive patch corresponding to positions where the meander coils are disposed are locally deformed, such that the shear waves are generated at the vibrating portion.

7. The vibrator of any one of claim 6, further comprising a wedge which is interposed between the waveguide and the bulk-type medium, and has a semi-cylindrical shape having a semicircular cross section and a length corresponding to a width of the waveguide that corresponds to the width direction of the vibrating portion,
wherein a contact surface at a lower end of the waveguide is formed as a curved surface corresponding to a curved surface of the wedge, and the shear waves are transmitted in a desired direction to the bulk-type medium when the contact surface of the waveguide is in contact with a desired position on the curved surface of the wedge.

8. The vibrator of claim 3, further comprising a wedge which is interposed between the waveguide and the bulk-type medium, and has a semi-cylindrical shape having a semicircular cross section and a length corresponding to a width direction of the waveguide,
wherein a contact surface at a lower end of the waveguide is formed as a curved surface corresponding to a curved surface of the wedge, and
the shear waves are transmitted in a desired direction to the bulk-type medium when the contact surface of the waveguide is in contact with a desired position on the curved surface of the wedge.

9. The vibrator of claim 8, wherein the wedge further comprises:
a link connecting portion which extends from a lower rectangular surface of the semi-cylindrical shape downward toward the bulk-type medium; and
a connecting link which is connected to both the link connecting portion and the waveguide and maintains the waveguide at a position on the wedge.

10. The vibrator of claim 3, wherein the transmitting portion is installed to contact the bulk-type medium while being used, and
an inclined surface inclined with respect to a longitudinal direction of the waveguide is formed at an end of the transmitting portion contacting the bulk-type medium.

11. The vibrator of claim 3, wherein a sound-absorbing material or a backing material preventing reflection of ultrasonic waves in the waveguide is further disposed in the vibrating portion.

12. A method of transmitting shear waves to a bulk-type medium by using a waveguide comprising a vibrating portion vibrated by a vibrating unit, a transmitting portion transmitting shear waves generated by the vibrating unit to a bulk-type medium and being thicker than the vibrating portion, and a connecting portion contacting both the vibrating portion and the transmitting portion and having a thickness varying from a portion contacting the vibrating portion to a portion contacting the transmitting portion, the method comprising:
deciding a pattern and a frequency of the shear waves to be transmitted to the bulk-type medium;
deciding a thickness of the transmitting portion of the waveguide corresponding to the decided pattern;
deciding a thickness of a plate generating only a first mode of the shear waves at the decided frequency, and setting the decided thickness of the plate as a thickness of the vibrating portion; and
connecting the transmitting portion of the waveguide to the bulk-type medium, and transmitting the shear waves to the vibrating portion by using the vibrating unit.

13. The method of claim 12, further comprising:
deciding a propagation direction of the shear waves to be transmitted to the bulk-type medium; and
installing a semi-cylindrical wedge between the transmitting portion and the bulk-type medium, contacting the transmitting portion of the waveguide with the semi-cylindrical wedge, and then disposing the waveguide in parallel to a direction in which the shear waves are to be transmitted.

* * * * *